(12) United States Patent
Guederian et al.

(10) Patent No.: US 8,048,161 B2
(45) Date of Patent: Nov. 1, 2011

(54) HYBRID GLENOID FOR SHOULDER ARTHROPLASTY

(75) Inventors: Gregory A. Guederian, Naples, FL (US); Anthony A. Romeo, Willowbrook, IL (US)

(73) Assignee: Arthex, Inc., Naples, FL (US)

( * ) Notice: Subject to any disclaimer, the term of this patent is extended or adjusted under 35 U.S.C. 154(b) by 224 days.

(21) Appl. No.: 12/265,584

(22) Filed: Nov. 5, 2008

(65) Prior Publication Data

US 2009/0125113 A1    May 14, 2009

Related U.S. Application Data

(60) Provisional application No. 60/986,215, filed on Nov. 7, 2007.

(51) Int. Cl.
*A61F 2/40* (2006.01)
(52) U.S. Cl. ............ 623/19.13; 623/19.11; 623/17.11
(58) Field of Classification Search ............ 623/17.11, 623/19.11, 19.13
See application file for complete search history.

(56) References Cited

U.S. PATENT DOCUMENTS

| | | | |
|---|---|---|---|
| 4,261,062 A | 4/1981 | Amstutz et al. |
| 4,964,865 A | 10/1990 | Burkhead et al. |
| 4,986,833 A | 1/1991 | Worland |
| 5,032,132 A | 7/1991 | Matsen, III et al. |
| 5,080,673 A | 1/1992 | Burkhead et al. |
| 5,489,310 A | 2/1996 | Mikhail |
| 5,593,448 A | 1/1997 | Dong |
| 5,702,447 A | 12/1997 | Walch et al. |
| 5,800,551 A | 9/1998 | Williamson et al. |
| 5,928,285 A | 7/1999 | Bigliani et al. |
| 6,228,119 B1 | 5/2001 | Ondrla et al. |
| 6,364,910 B1 | 4/2002 | Shultz et al. |
| 6,379,386 B1 | 4/2002 | Resch et al. |
| 6,406,495 B1 | 6/2002 | Schoch |
| 6,514,287 B2 | 2/2003 | Ondrla et al. |
| 6,673,115 B2 | 1/2004 | Resch et al. |
| 6,911,047 B2 | 6/2005 | Rockwood, Jr. et al. |

(Continued)

FOREIGN PATENT DOCUMENTS

EP    0 538 895 A2    4/1993

(Continued)

OTHER PUBLICATIONS

Kimitaka Fukuda, M.D., Chang-Ming Chen, B.S., Robert H. Cofield, M.D., and Edmund Y.S, Chao, Ph.D., *Biomechanical Analysis of Stability and Fixation Strength of toal Shoulder Prostheses*, 1988, pp. 141-149, vol. 11, No. 1 (Jan.), Orthopedics, Mayo Foundation, Rochester, Minnesota.

(Continued)

*Primary Examiner* — Thomas J Sweet
*Assistant Examiner* — Seema Swaminathan
(74) *Attorney, Agent, or Firm* — Dickstein Shapiro LLP

(57) ABSTRACT

Glenoid prosthesis with a hybrid design (combining both peg and keel designs), and surgical methods for reconstitution of a shoulder joint. The hybrid design combines both peg and keel components into one device. The hybrid glenoid component of a shoulder prosthesis includes an oval body having a concave lateral articulating surface and an opposing convex medial surface. The medial surface is provided with a plurality of pegs and a single inferior protrusion. The pegs are used to attain both a superior location as well as a central location. The inferior protrusion provides stability in the superior-to-inferior translation of the humeral head, as well as rotational articulation of the same.

7 Claims, 3 Drawing Sheets

U.S. PATENT DOCUMENTS

| | | | |
|---|---|---|---|
| 7,160,328 | B2 | 1/2007 | Rockwood, Jr. et al. |
| 7,204,854 | B2 | 4/2007 | Guederian et al. |
| 7,294,149 | B2 | 11/2007 | Hozack et al. |
| 7,329,284 | B2 | 2/2008 | Maroney et al. |
| 2001/0037153 | A1 | 11/2001 | Rockwood, Jr. et al. |
| 2003/0125809 | A1 | 7/2003 | Iannotti et al. |
| 2005/0049709 | A1 | 3/2005 | Tornier |
| 2005/0060039 | A1 | 3/2005 | Cyprien |
| 2005/0261775 | A1 | 11/2005 | Baum et al. |
| 2006/0069443 | A1 | 3/2006 | Deffenbaugh et al. |
| 2006/0069444 | A1 * | 3/2006 | Deffenbaugh ............. 623/19.11 |
| 2006/0079963 | A1 | 4/2006 | Hansen |
| 2006/0111787 | A1 | 5/2006 | Bailie et al. |
| 2006/0122705 | A1 | 6/2006 | Morgan |
| 2006/0149388 | A1 | 7/2006 | Smith et al. |
| 2006/0195194 | A1 | 8/2006 | Gunther |
| 2007/0016304 | A1 | 1/2007 | Chudik |
| 2007/0038302 | A1 | 2/2007 | Shultz et al. |
| 2007/0055380 | A1 | 3/2007 | Berelsman et al. |
| 2007/0118227 | A1 | 5/2007 | King et al. |
| 2007/0142917 | A1 | 6/2007 | Rocher et al. |
| 2007/0219637 | A1 | 9/2007 | Berelsman et al. |
| 2007/0219638 | A1 | 9/2007 | Jones et al. |
| 2007/0225817 | A1 | 9/2007 | Reubelt et al. |
| 2007/0244564 | A1 | 10/2007 | Ferrand et al. |

FOREIGN PATENT DOCUMENTS

| | | |
|---|---|---|
| EP | 0 608 997 A1 | 8/1994 |
| EP | 0 679 375 A1 | 11/1995 |
| EP | 1 402 854 A2 | 3/2004 |
| FR | 2 377 798 | 8/1978 |
| FR | 2 776 506 | 10/1999 |
| FR | 2 843 293 B1 | 1/2005 |
| WO | WO 95/30389 | 11/1995 |
| WO | WO 02/39931 A1 | 5/2002 |
| WO | WO 2007/109291 A2 | 9/2007 |

OTHER PUBLICATIONS

Melvin Post, *Constrained Arthroplasty of the Shoulder*, The Orthopedic Clinics of North America, 1987, pp. 455-462, vol. 18, No. 3, Elsevier Mosby Saunders, Philadelphia, Pennsylvania.

Joseph D. Zuckerman, M.D., and Frederick A. Matsen III, M.D., *Complications about the Glenohumeral Joint Related to the Use of Screws and Staples*, The Journal of Bone and Joint Surgery, 1984, pp. 175-180, vol. 66, No. 2, The Journal of Bone and Joint Surgery, Needham, Massachusetts.

Robert H. Cofield, M.D., *Total Joint Arthroplasty the Shoulder*, Mayo Clinic Proceedings, 1979, pp. 500-506, vol. 54, No. 8, Mayo Foundation, Rochester, Minnesota.

Ove Engkvist, *Reconstruction of Patellar Articular Cartilage With Free Autologous Perichondrial Grafts, An Experimental Study in Dogs*, Scandinavian Journal of Plastic and Reconstructive Surgery and Hand Surgery, 1979, pp. 361-369, vol. 13, No. 2, Informa Healthcare, London, England, United Kingdom.

Raja Kummoona, B.D.S., *Functional Rehablitation of Ankylosed Temporomandubular Joints*, Oral Surgery, Oral Medicine and Oral Pathology, 1978, pp. 495-505, vol. 46, No. 4 (Oct.), Elsevier Mosby Saunders, Philadelphia, Pennsylvania.

Mary Hughes, B.S., and Charles S. Neer II, M.D., *Glenhumeral Joint Replacement and Postoperative Rehabilitation*, Physical Therapy, 1975, pp. 850-858, vol. 55, No. 8 (Aug.), American Physical Therapy Association, Alexandria, Virginia.

* cited by examiner

HYBRID GLENOID FOR SHOULDER ARTHROPLASTY

CROSS-REFERENCE TO RELATED APPLICATIONS

This application claims the benefit of U.S. Provisional Application No. 60/986,215, filed Nov. 7, 2007, the entire disclosure of which is incorporated by reference herein.

FIELD OF THE INVENTION

The present invention relates to surgical reconstitution of the shoulder and, in particular, to prosthetic replacement of the glenoid.

BACKGROUND OF THE INVENTION

Shoulder instability and other maladies of the shoulder joint, such as arthrosis or fracture, can be sufficiently acute that prosthetic replacement of compromised joint features may be indicated. Such prosthetic replacement typically has a humeral component and a corresponding glenoid component.

Glenoid components for artificial shoulder joint typically follow two predominant designs: peg and keel. The peg glenoids are generally known for their stability (multiple pegs distributed about the medial surface). Pegs are also favored for minimal bone loss due to machining. Keel glenoids are generally positioned longitudinally (superior to inferior). Although both glenoid designs are currently used in the art, there is no current clinical evidence proving that either of the two designs is superior.

SUMMARY OF THE INVENTION

The present invention provides a glenoid prosthesis with a hybrid design (combining both peg and keel designs), and surgical methods for reconstitution of a shoulder joint. The hybrid design combines both peg and keel components into one device.

The present invention also provides surgical methods for reconstitution of a shoulder joint. According to an exemplary embodiment, the method of shoulder joint reconstruction of the present invention comprises the steps of: (i) providing a glenoid module having a hybrid design that combines both peg and keel designs; and (ii) operatively connecting the glenoid module to the scapula and the humerus.

These and other features and advantages of the invention will be more apparent from the following detailed description that is provided in connection with the accompanying drawings and illustrated exemplary embodiments of the invention.

DETAILED DESCRIPTION OF THE PREFERRED EMBODIMENTS

In the following detailed description, reference is made to various specific embodiments in which the invention may be practiced. These embodiments are described with sufficient detail to enable those skilled in the art to practice the invention, and it is to be understood that other embodiments may be employed, and that structural and logical changes may be made without departing from the spirit or scope of the present invention.

The present invention provides glenoid prosthesis with a hybrid design (combining both peg and keel designs), and surgical methods for reconstitution of a shoulder joint. The hybrid design combines both peg and keel components into one device.

In an exemplary embodiment, the hybrid glenoid component of a shoulder prosthesis of the present invention includes an oval body having a concave lateral articulating surface and an opposing convex medial surface. The medial surface is provided with a plurality of pegs and an inferior protrusion. In the hybrid design of the present invention, the pegs are used to attain both a superior location as well as a central location. The inferior protrusion provides stability in the superior-to-inferior translation of the humeral head, as well as rotational articulation of the same.

The prosthetic glenoid component of the present invention attaches to a glenoid surface of a scapula to replace a natural socket of a shoulder and provides a bearing surface for a head portion of an arm bone or humerus. As detailed below, the prosthetic glenoid component of the present invention is provided with integrally formed attachment legs or pegs (which may be cemented into corresponding holes formed in the glenoid surface), and also with a protrusion (extending from the medial surface of the device) which may be also cemented into a corresponding hole or depression in the glenoid surface.

Figure 1:
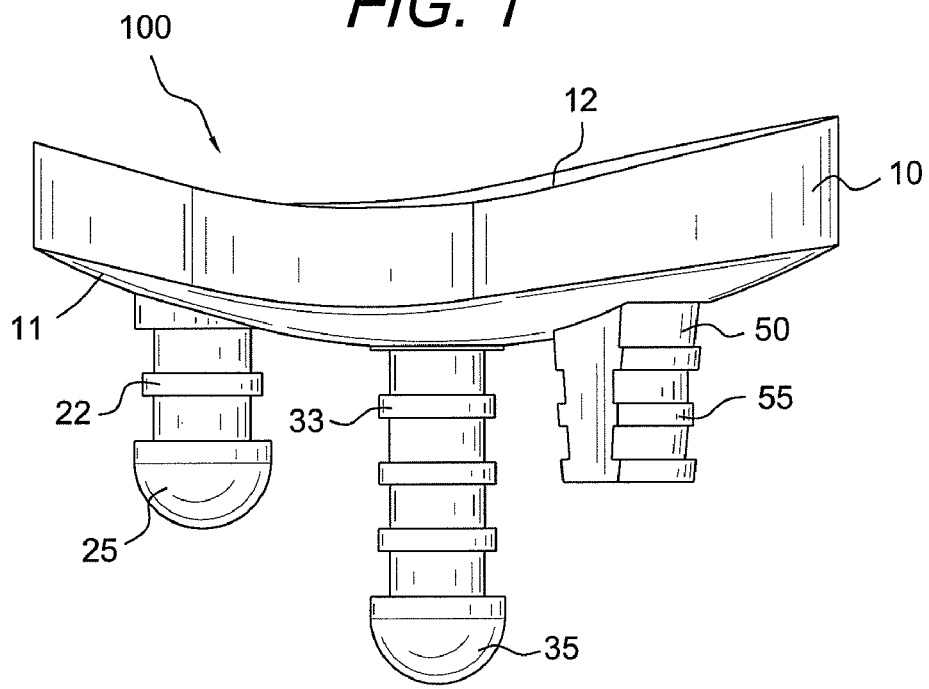
FIG. 1 illustrates a lateral view of a hybrid glenoid component of an artificial shoulder joint in accordance with an exemplary embodiment of the present invention.
Figure 2:
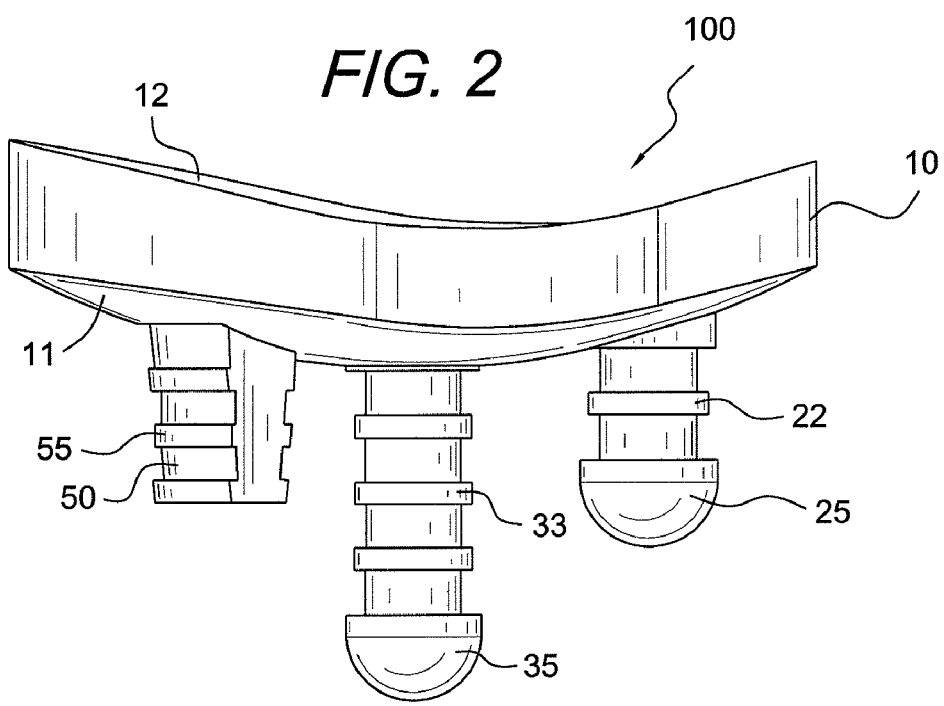
FIG. 2 is a lateral view of the hybrid glenoid component of FIG. 1 rotated 180 degrees.
Figure 3:
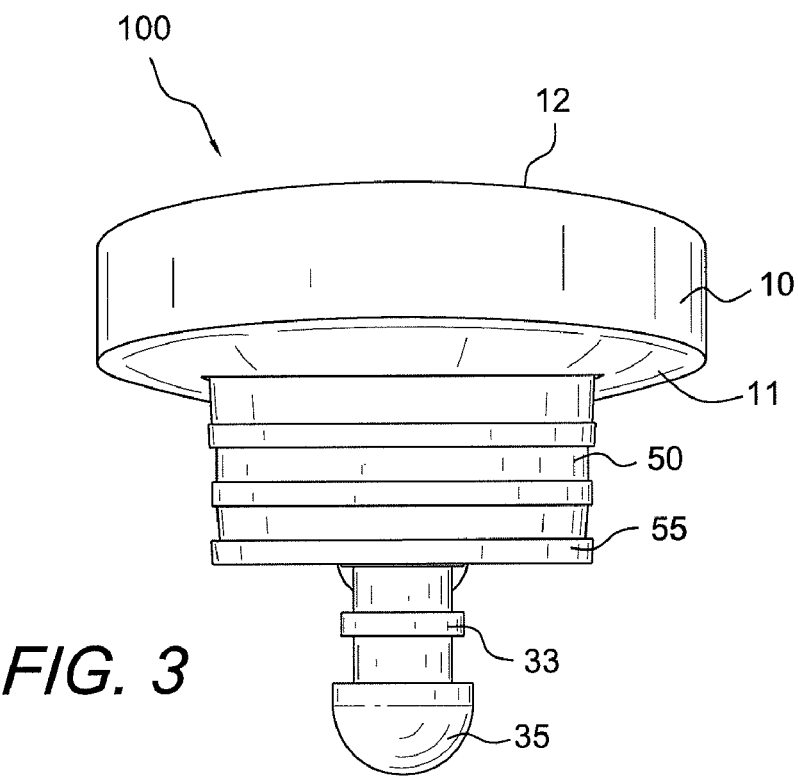
FIG. 3 is a lateral view of the hybrid glenoid component of FIG. 1 rotated 90 degrees.
Figure 4:
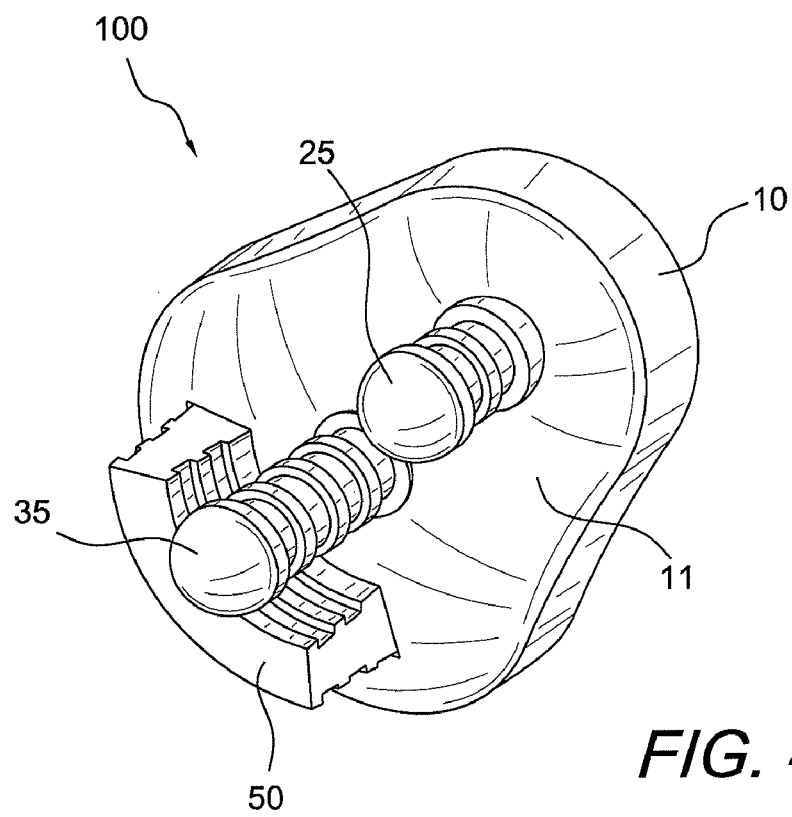
FIG. 4 is a perspective elevational view of the hybrid glenoid component of FIG. 1.
Figure 5A:
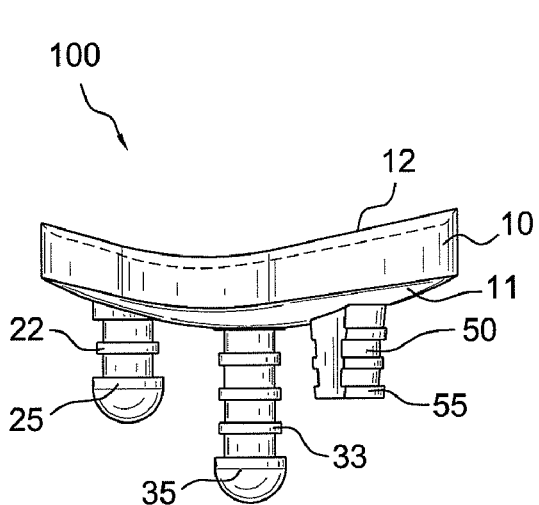
FIGS. 5(a)-(d) illustrate additional views of the hybrid glenoid component of FIG. 1.
Figure 5B:
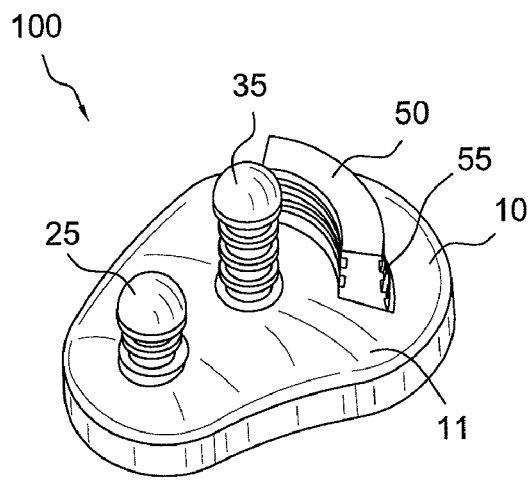
Figure 5C:
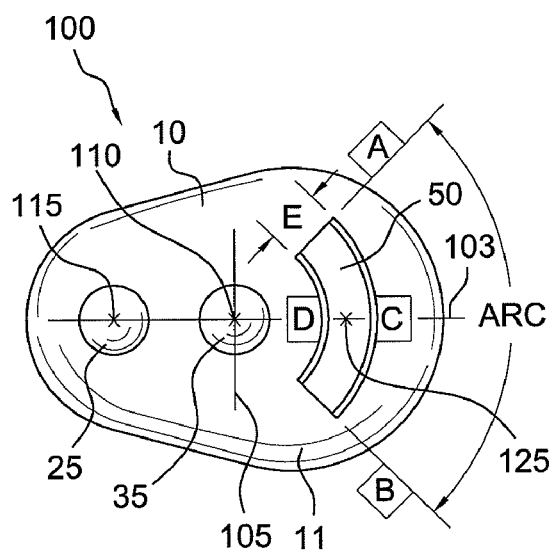
Figure 5D:
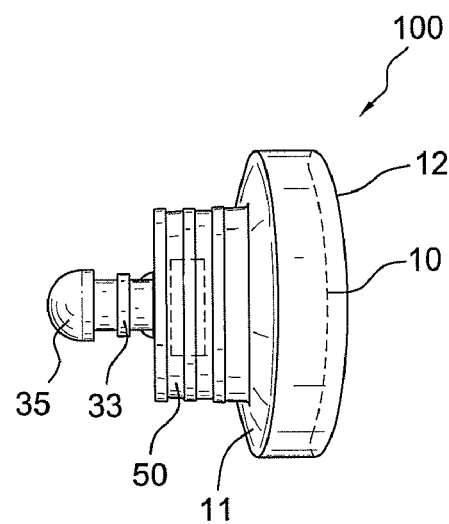

Referring now to the drawings, where like elements are designated by like reference numerals, FIGS. 1-5 illustrate exemplary embodiments of glenoid prosthesis 100 of the present invention comprising an oval body 10 provided with at least one attachment leg or peg (for example, a plurality of pegs 25, 35) and at least one protrusion (for example, a single protrusion 50) extending from the medial surface of the glenoid prosthesis 100.

In an exemplary embodiment, the glenoid component 100 includes an oval body 10 having a concave lateral articulating surface 12 (the humeral facing side), and an opposing convex medial surface 11 (the scapular facing side). Oval body 10 is formed to be approximately the same shape as a natural glenoid cavity. Articulating surface 12 provides a bearing surface for the head portion of the humeral component.

As illustrated in the drawings, convex medial surface 11 of oval body 10 is provided with a plurality of attachment legs, posts or pegs 25, 35 and a single protrusion 50 extending from the medial surface of the device 100. The pegs 25, are used to attain a superior location as well as central location. The inferior protrusion 50 provides stability in the superior-to-inferior translation of the humeral head, as well as rotational articulation of the same.

According to an exemplary embodiment only, a single superior peg 25 and a single central peg 35 are provided on the convex medial surface 11 of oval body 10 of the hybrid glenoid 100. In exemplary embodiments, each peg 25, 35 may be provided with multiple annular rings or barbs 22, 33 which are spaced along the longitudinal length of the peg to provide an increased bonding area for the cement or bonding material.

The annular rings or barbs 22, 33 may have various geometries and configurations, and may be provided with a variety of cross-sections (for example, barb, square and/or round, among others) or a combination of such cross-sections. These rings and/or barbs are designed to hold a maximum amount of cement or bonding material (when the device is impacted into a cement-filled glenoid slot) and to improve, therefore, the pull out characteristics of the hybrid glenoid prosthesis 100. The pegs 25, 35 may be provided about perpendicular to the oval body 10 of glenoid prosthesis 100 (i.e., forming an angle of about 90 degrees with a tangent to the surface 11 of the device) or may form an oblique angle (or different oblique angles) to the articulating surface 11.

According to an exemplary embodiment only, a single inferior protrusion 50 having a radial configuration is provided on the convex medial surface 11 of oval body 10 of the hybrid glenoid prosthesis 100. The inferior protrusion 50 may have a partially-circular cross-section (i.e., an arcuate cross-section), as illustrated in FIGS. 5(*b*) and 5(*c*), for example. The cross-sectional geometry of protrusion 50 may include a series of protuberances 55 (for example, barb, square and/or round forms, or any combination thereof). Single or multiple fenestrations (having various geometries and configurations) may be also provided through the protrusion 50, if desired. As shown in FIG. 5(*c*), the included angle radius of the protrusion 50 formed between surface "A" and surface "B" is preferably greater than about 1 degree and preferably smaller than about 180 degrees. The width of the protrusion 50 is designated as "E" in FIG. 5(*c*) and is formed between surface "C" and "D." Radius "C" and radius "D" may or may not be concentric to each other. Protrusion 50 may be also provided about perpendicular to the oval body 10 of glenoid prosthesis 100 (i.e., forming an angle of about 90 degrees with a tangent to the surface 11 of the device) or may form an oblique angle to the articulating surface 11.

According to an exemplary embodiment, and as shown in FIG. 5(*c*), the center of each of the pegs 25, 35 and of the protrusion 50 are positioned on the superior-inferior centerline 103. In addition, the center of one of the pegs 25, 35 (for example, the center of peg 35) may coincide with center 110 of the oval body 10 (which is where the superior-inferior centerline 103 intersects the anterior-posterior centerline 105). Preferably, center 115 of peg 25 and center 125 of the protrusion 50 are positioned on the superior-inferior centerline 103 an equal distance from the center 110.

The medial surface 11 of body 10 may be constructed of one or several intersecting surfaces to form a generally convex shape.

The glenoid component 100 of the present invention may be employed in a total shoulder replacement procedure. In a total shoulder replacement procedure, a humeral component having a head portion is used to replace the natural head portion of the humerus. The humeral component typically has an elongated intramedullary stem to secure the humeral component to the humerus. The glenoid portion of the scapula is resurfaced with a glenoid component which provides a bearing surface for the head portion of the humeral component. For example, the glenoid prosthesis 100 can be positioned in a resected portion of the head of the scapula.

An exemplary and only illustrative method of employing the hybrid design of the glenoid component 100 (combining both pegs and keel into one device) for shoulder joint reconstruction is detailed below with reference to the following steps:

Exposure to the glenoid is initially performed. A template with central hole is applied to the lateral aspect of the glenoid. A hole is drilled into the glenoid bone. The template is removed. A spherical reamer with a central pin is located and aligned to the previously-drilled hole. The lateral surface of the bone is machined to the approximate geometry of the convex glenoid surface. A second template, having a central pin, a single superior hole, and multiple inferior holes which are arranged in a radial pattern, is located and aligned to the previously-drilled hole. The superior hole is not drilled. A peg device is inserted into the superior hole which allows the template to maintain its position. A series of inferiorly placed holes, radially positioned, are drilled. The peg is removed from the superior hole. The template is removed from the glenoid.

Small bone bridges which are residual to the drilling of the radial hole pattern are excised using a small ronguer. A dilator in the shape of the radial protrusion is impacted into the cavity formed by the previous drilling procedure. The function of the dilator is to remove and compact bone.

Cement is applied to any or all cavities created as a result of the machining process. Cement may also be applied to surfaces of the glenoid component 100 which may come in contact with bone. The glenoid component 100 is aligned to the previously-formed cavities with the assistance of a manipulation instrument. The glenoid prosthesis 100 is then impacted into place.

The advantage of the hybrid design of the glenoid component 100 of the present invention is found in the combination of both pegs and keel into one device. The pegs 25, 35 are used to obtain superior and central locations, which are difficult to attain. The inferior protrusion 50 provides stability in the superior to inferior translation of the humeral head, as well as rotational articulation of the same.

Although the present invention has been described in connection with preferred embodiments, many modifications and variations will become apparent to those skilled in the art. While preferred embodiments of the invention have been described and illustrated above, it should be understood that these are exemplary of the invention and are not to be considered as limiting. Accordingly, it is not intended that the present invention be limited to the illustrated embodiments, but only by the appended claims.

What is claimed as new and desired to be protected by Letters Patent of the United States is:

1. A glenoid prosthesis providing affixation to a resected surface of a scapula, the glenoid prosthesis comprising:

an oval body having an inferior-superior axis, a lateral surface operatively connected to a humeral head, and a medial surface for attaching to the resected surface of a scapula;

a plurality of pegs extending medially from the medial surface for insertion into the resected surface of a scapula, each of the plurality of pegs having a plurality of circumferential barbs or grooves; and at least one protrusion having an elongated arcuate cross-section in a plane parallel to the medial surface, the protrusion extending medially from the medial surface, and disposed laterally of the plurality of pegs, for insertion into the resected surface of the scapula, wherein the centers of each of the plurality of pegs and of the at least one protrusion are located on the inferior-superior axis of the body.

2. The glenoid prosthesis of claim 1, wherein at least one of the plurality of pegs extends from the medial surface at an oblique angle to the articulating surface.

3. The glenoid prosthesis of claim 1, wherein the at least one protrusion is provided with fenestrations.

4. The glenoid prosthesis of claim 1, wherein the at least one protrusion is provided with barbs.

5. The glenoid prosthesis of claim 1, wherein the body, the plurality of pegs and the at least one protrusion form an integral device.

6. The glenoid prosthesis of claim 1, wherein at least one peg and at least one protrusion are spaced on the inferior-superior axis about equal distance from the center point.

7. The glenoid prosthesis of claim 1, wherein the body comprises ultra-high molecular weight polyethylene.

* * * * *